(12) United States Patent
LaTorre et al.

(10) Patent No.: US 6,517,863 B1
(45) Date of Patent: Feb. 11, 2003

(54) COMPOSITIONS AND METHODS FOR TREATING NAILS AND ADJACENT TISSUES

(75) Inventors: Guy LaTorre, Gainesville, FL (US); David C. Greenspan, Gainesville, FL (US); Alice D. Greenspan, Gainesville, FL (US)

(73) Assignee: USBiomaterials Corporation, Alachua, FL (US)

( * ) Notice: Subject to any disclaimer, the term of this patent is extended or adjusted under 35 U.S.C. 154(b) by 0 days.

(21) Appl. No.: 09/488,202

(22) Filed: Jan. 19, 2000

Related U.S. Application Data

(60) Provisional application No. 60/116,595, filed on Jan. 20, 1999.

(51) Int. Cl.$^7$ .......................... A61L 15/16; A61F 13/00
(52) U.S. Cl. .................. 424/447; 424/405; 424/443; 424/445; 424/446; 424/61; 514/722.4
(58) Field of Search ........................ 424/61, 405, 443, 424/445, 446, 447; 514/722.4

(56) References Cited

U.S. PATENT DOCUMENTS

| | | | |
|---|---|---|---|
| 3,234,097 A | 2/1966 | Loughran et al. | 167/85 |
| 3,725,525 A | 4/1973 | Joos | 424/61 |
| 3,914,405 A | * 10/1975 | Shephard et al. | |

(List continued on next page.)

FOREIGN PATENT DOCUMENTS

| | | |
|---|---|---|
| WO | 92/21628 | 7/1996 |
| WO | 97/27148 | 7/1997 |

OTHER PUBLICATIONS

Hench, L. L., and Wilson, J., "Bioceramics", *MRS Bulletin*, 62–74, Sep., 1991.

Ogina, M., et al., "Compositional dependence of the formation of calcium phosphate films on bioglass", *J. Of Biomedical Materials Research*, (John Wiley & Sons, Inc.) 14: 55–64, 1980.

Dawber, R.P.R., et al, " Structure, Embryology, Comparative Anatomy and Phsiology of the Nail", *Diseases of the Nails and Their Management*, 1: 1–23, 1983.

Hench, L. L., et al., "Bonding Mechanisms at the Interface of Ceramic Prosthetic Materials," *J. Biomed Mater. Res. Syn.*, 2(1):117–141, 1971.

Hench, L. L., "Handbook of Bioactive Ceramics," CRC, 1:235–244 and 283–302, 1990.

Kim, C.Y., et al., "Early Stages of Calcium= Phosphate Layer Formation in Bioglass", *J. Non–Cryst. Solids*, 113:195–202 (1999).

**Pantard, F.G.E., "Progress in Biological Sciences in Relation to Dermatology", 2:227, ed. Rooks and Champion, Cambridge University Press, London,1964.

(List continued on next page.)

*Primary Examiner*—Thurman K. Page
*Assistant Examiner*—Rachel M. Bennett
(74) *Attorney, Agent, or Firm*—Burns, Doane, Swecker & Mathis, L.L.P.

(57) ABSTRACT

Compositions and methods for treating nails and adjacent tissues are disclosed. The compositions include non-interlinked particles of bioactive glass, alone or in combination with therapeutic agents, hydrophilic polymers, and other optional components. The compositions optionally include an appropriate aqueous carrier for topical administration. The methods involve applying an effective nail-enhancing amount of the composition to the nails and adjacent tissues for a sufficient amount of time to cause the formation of a hydroxyapatite or other calcium phosphate mineral layer on the nail surface.

16 Claims, 4 Drawing Sheets

Bioactive Glasses in Nail Care Applications
Experiment #2(soak): SEM Analysis

Unreacted nail surface

U.S. PATENT DOCUMENTS

| | | | |
|---|---|---|---|
| 3,969,128 A | 7/1976 | Urs | 106/291 |
| 3,989,817 A | 11/1976 | Mayer | 424/61 |
| 4,103,002 A | 7/1978 | Hench et al. | 428/155 |
| 4,115,307 A | 9/1978 | McGilvery | 252/135 |
| 4,159,358 A | 6/1979 | Hench et al. | 427/318 |
| 4,171,544 A | 10/1979 | Hench et al. | 3/1.9 |
| 4,189,325 A | 2/1980 | Barrett et al. | 106/35 |
| 4,234,972 A | 11/1980 | Hench et al. | 3/2.9 |
| 4,482,538 A | 11/1984 | Davies | 424/61 |
| 4,547,363 A | 10/1985 | Joos | 424/61 |
| 4,775,646 A | 10/1988 | Hench et al. | 501/2 |
| 4,851,046 A | 7/1989 | Low et al. | 106/35 |
| 4,873,077 A | 10/1989 | Thompson et al. | 424/61 |
| 4,919,920 A | 4/1990 | Devos | 424/61 |
| 5,074,916 A | 12/1991 | Hench et al. | 106/35 |
| 5,165,915 A | 11/1992 | Tokubo et al. | 424/63 |
| 5,166,168 A | 11/1992 | Stiefel | 514/387 |
| 5,181,914 A * | 1/1993 | Zook | |
| 5,403,402 A * | 4/1995 | LeGrow | |
| 5,410,016 A | 4/1995 | Hubbell et al. | 528/354 |
| 5,478,551 A | 12/1995 | Busch, Jr. | 424/61 |
| 5,508,027 A * | 4/1996 | Witbeck | |
| 5,658,184 A | 8/1997 | Hoopman et al. | 451/28 |
| 5,676,745 A | 10/1997 | Kelly et al. | 106/35 |
| 5,728,753 A * | 3/1998 | Bonfield | |
| 5,735,942 A | 4/1998 | Litkowski et al. | 106/35 |
| 5,785,959 A | 7/1998 | Wolf et al. | 424/61 |
| 5,814,305 A | 9/1998 | Laugier et al. | 424/61 |
| 5,834,008 A | 11/1998 | Greenspan et al. | 424/443 |
| 5,989,575 A | 11/1999 | Razzano | 424/401 |
| 6,428,800 B2 * | 8/2002 | Greenspan | |

OTHER PUBLICATIONS

Stanley, H. R., et al, "Residual alveolar ridge maintenance with a new endosseous implant material," *J. Prosthetic Dent.*, 58(5):607–613, 1987.

West, J.K., et al., "Reaction Kinetics of bioactive Ceramics Part V: Molecular Orbital Modeling of Bioactive Glass surface Ractions" *Bioceramics*, 5: 75–86, 1992.

Wilson, J., et al., "Biomaterials for facial bone augmentation: Comparative Studies," *J. Biomed. Mater. Res.*, 22 (A2):159–177, 1988.

Wilson J. et al., "Toxicology and Biocompatibility of Bioglasses," *J. Biomed. Mater. Res.*, 15: 805–817, 1981.

*Advanced Series in Ceramics—vol. 1, An Introduction to Bioceramics*, Hench & Wilson, Eds., World Scientific (1993).

* cited by examiner

COMPOSITIONS AND METHODS FOR TREATING NAILS AND ADJACENT TISSUES

This application claims priority under 35 U.S.C. §119 and/or 365 to U.S. provisional application No. 60/116,595 filed in U.S. on Jan. 20, 1999; the entire content of which is hereby incorporated by reference.

FIELD OF THE INVENTION

The present invention relates to compositions and methods for use in treating nails and adjacent tissues.

BACKGROUND OF THE INVENTION

The fingernails and toenails of humans are composed of clear, horny cells of the epidermis, joined so as to form a solid, continuous plate upon the dorsal surface of the terminal phalanges. Each nail is closely adherent to the underlying corium, which is modified to form what is called the nail bed, or matrix. The body of the nail is the part that shows. The hidden part, in the nail groove, is called the root.

The nails grow in length by multiplication of the soft cells (corneocytes) in the stratum germinativum at the root. The cells are transformed into hard, dry scales, which unite to form a solid plate; and the nail, constantly receiving additions, slides forward over its bed and projects beyond the end of the finger.

Keratin fibrils found within the corneocytes provide strength and flexibility to the cells due to the presence of cysteine disulfide bridges, which are found at a level of about 9.4% by weight in the nail. In addition, the intercellular adhesive factors which hold corneocytes together also provide strength and flexibility. These intercellular adhesive factors are intercellular cement, desmosomes, and gap junctions and narrow junctions.

The nails often become brittle or damaged from a variety of exposures including washing and cleaning agents, organic solvents in nail polishes and nail polish removers, dehydration, bacterial or fungal infections, injuries and aging. As a result, a variety of approaches have been used to strengthen and harden nails, including the application of enamel coatings, lotions, oils and adhesives.

Numerous nail hardening or strengthening compositions have been marketed with varying results. In most cases, these compositions include ingredients that do not interact directly with the nail, but are protective coatings which are applied to the surface of the nail. There is a need for nail strengthening compositions that are capable of interacting with the nail to enhance nail strength without using organic solvents and other chemicals which can ultimately damage the nail.

Approaches in the use of traditional nail hardening agents that are applied as protective coating for the nail body have been described. For example, U.S. Pat. No. 5,508,027 discloses methods and compositions for strengthening nails (ungues) by the periodic application of synthetic gums of acrylic polymer films on the nail body. These acrylic polymer films are aqueous-based and avoid using the harmful organic solvents commonly found in other nail polish products. While this approach eliminates the use of harmful solvents, the composition must be applied from 1 to 5 times a day to 1 to 3 times a week over a period of at least a month to be effective.

U.S. Pat. Nos. 4,873,077 and 4,482,538 disclose preparations for strengthening nails by using hardener compositions. The compositions include a nitrocellulose-based lacquer and inert glass fibers or beads. The inert glass fibers or beads act as a reinforcement phase that increases the strength and wear resistance of the coatings of the nails relative to a conventional lacquer film alone. A limitation of this approach is that the compositions use organic solvents which can be detrimental to nail health, and the compositions do not increase the strength of the nail itself.

Nail hardening agents have been developed which interact with the nail body. For example, U.S. Pat. No. 5,785,959 discloses using a three part nail strengthening composition which penetrates and interacts with the nail and enhances the binding of water or lipids from the nail bed. This results in water retention within the nail, which reduces the brittleness of the nail resulting from decreased moisture content.

U.S. Pat. No. 4,919,920 discloses compositions and methods for hardening and strengthening the keratinized appendages of mammals by topically applying fluoride ions in an aqueous cosmetic vehicle. The use of fluoride ions simultaneously hardens and strengthens the nail. U.S. Pat. No. 5,478,551 discloses compositions and methods for strengthening nails by using a non-aqueous organic composition containing ammonium hexafluorophosphate to provide an effective amount of fluoride to the nail body. Both of these approaches can potentially form harmful acidic by-products, and the second approach uses organic solvents, both of which can damage the nail body and irritate the surrounding tissues.

It would be advantageous to provide compositions and methods of treating nails in humans (as well as other mammals) and surrounding tissues which avoid using organic solvents and which also avoid creating acidic by-products. The present invention provides such compositions and methods.

SUMMARY OF THE INVENTION

Compositions and methods for treating nails and adjacent tissues are disclosed. Formulations including the compositions and a suitable topical carrier are also disclosed. The compositions include non-interlinked particles of bioactive glass or glass-ceramic, optionally include an aqueous vehicle, and further optionally include a hydrophilic polymer. The methods involve applying an effective nail-enhancing amount of the composition to the nail body for a sufficient amount of time such that a layer of hydroxyapatite or other calcium phosphate crystals is formed on the nail and ions from the glass penetrate the layers of the nail to form hydroxyapatite crystals within the layers of the nail.

When the compositions are in the form of aqueous solutions, the methods involve soaking the nails in the solutions for a sufficient period of time to create a layer of hydroxyapatite or other calcium phosphate mineral on the nail and allows calcium and phosphate ions to penetrate through the porous outer surface of the nail into the body of the nail and form apatite or other calcium phosphate crystals. When the composition is in the form of a gel (i.e., includes a hydrophilic polymer), the compositions can be applied to the nail and can remain on the nail bed until the gel is wiped off. In one embodiment, the hydrophilic polymer includes a polymerizable group which is polymerized when the composition is applied to the nail bed to facilitate maintaining the composition in contact with the nail bed.

In one embodiment, the compositions can include additional components, such as antibiotics, antivirals, anti-fungal agents, biotin, collagen, amino acids, proteins, vitamins, penetration enhancers and/or permeation/binding agents, dyes, fragrances and other cosmetically useful additives. Bioactive glass also has anti-microbial properties.

The compositions and methods allow one to enhance the hardness and durability of the nail body and also the health of the surrounding tissues. The compositions form a protective layer of hydroxyapatite or other calcium phosphate mineral on the nail body, which effectively hardens and increases the durability of the nail.

DETAILED DESCRIPTION OF THE PREFERRED EMBODIMENTS

Figure 1A:
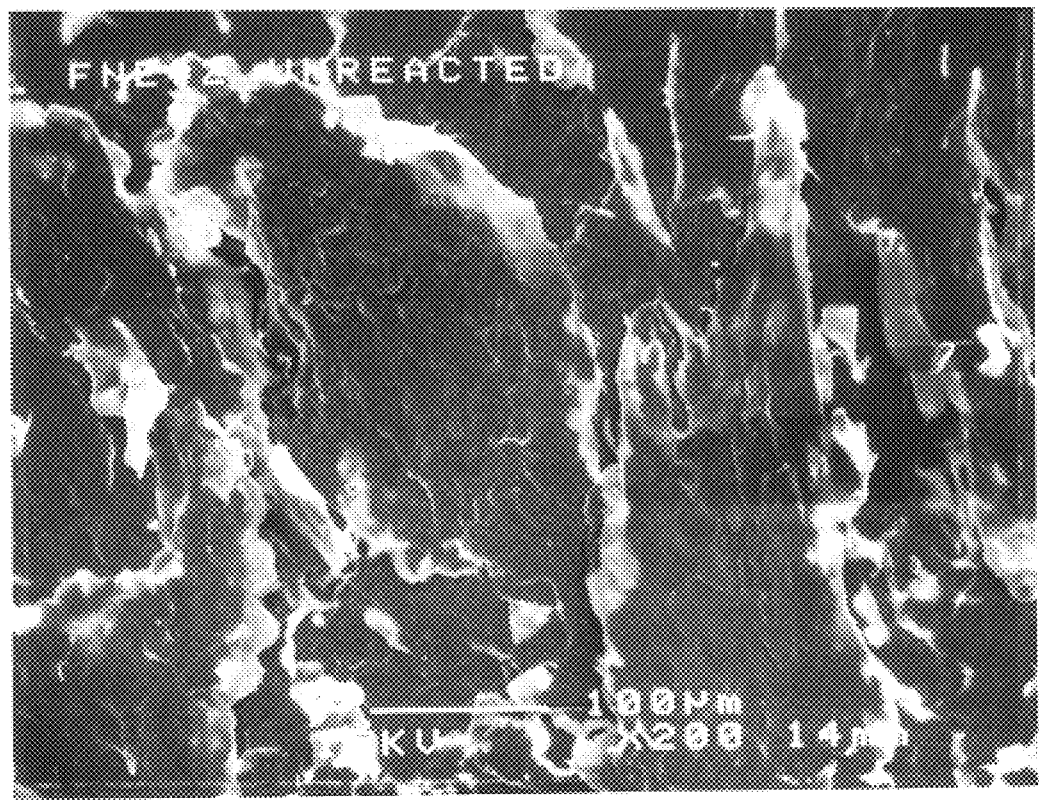
FIGS. 1a and 1b are scanning electron micrographs (SEMs) (200× magnification) of an untreated fingernail (FIG. 1a) and a nail treated for 20 hours with a TRIS buffer solution including Bioglass® particles (FIG. 1b).

Compositions and methods for treating nails and adjacent tissues are disclosed. These compositions and methods are useful in humans and mammals other than humans such as dogs and cats. Formulations including the composition and a suitable carrier, preferably for topical administration, are also disclosed.

The compositions include an effective, nail-enhancing amount of non-interlinked particles of bioactive glass, optionally include an aqueous, topical carrier, and further optionally include a hydrophilic polymer. An effective, nail-enhancing amount of bioactive glass is defined as an amount capable of providing the nail surface with at least a thin coating of hydroxyapatite. A thin coating of hydroxyapatite is defined as a layer at least about 0.2 microns thick. The coating layers are typically between about 0.2 and 3 microns thick but can be as much as 20 microns thick.

Not being bound to any particular theory or mechanism, it is believed that the surface area and reactivity of particulate bioactive glass provides an adsorption of hydronium ions from a solution and a release of sodium and/or calcium ions that increases the pH of the environment. This is followed by the release, over an extended period of time, of calcium and phosphate ions, which become available to form the calcium phosphate layer and/or to penetrate into the nail body. These reactions also develop a higher negative surface charge on the glass surface and develop a high specific surface area which provides for the rapid formation of a calcium and phosphate layer on the nail.

I. Compositions Including Bioactive Glass

As used herein the terms "bioactive glass" or "biologically active glass" mean an inorganic glass material having an oxide of silicon as its major component and which is capable of bonding with growing tissue when reacted with physiological fluids.

Bioactive glasses are well known to those skilled in the art, and are disclosed, for example, in *An Introduction to Bioceramics*, L. Hench and J. Wilson, eds. World Scientific, New Jersey (1993), the contents of which are hereby incorporated by reference.

The glass preferably includes between 40 and 86% by weight of silicon dioxide oxide ($SiO_2$), between about 0 and 35% by weight of sodium oxide ($Na_2O$), between about 4 and 46% by weight calcium oxide (CaO), and between about 1 and 15% by weight phosphorus oxide ($P_2O_5$). More preferably, the glass includes between 40 and 68% by weight of silicon dioxide ($SiO_2$), between about 5–30% by weight of sodium oxide ($Na_2O$), between about 10 and 35% by weight calcium oxide (CaO), and between about 1 and 12% by weight phosphorus oxide ($P_2O_5$). The oxides can be present as solid solutions or mixed oxides, or as mixtures of oxides.

$CaF_2$, $B_2O_3$, $Al_2O_3$, MgO and $K_2O$ may be included in the composition in addition to silicon, sodium, phosphorus and calcium oxides. The preferred range for $B_2O_3$ is between 0 and 10% by weight. The preferred range for $K_2O$ is between 0 and 8% by weight. The preferred range for MgO is between 0 and 5% by weight.

The most preferred glass is Bioglass® (a trademark of University of Florida), which has a composition including about 45% by weight silicon dioxide, about 24.5% by weight sodium oxide, about 6% by weight phosphorus oxide, and about 24.5% by weight calcium oxide. Another preferred material is hydroxyapatite or other calcium phosphate minerals. Those of skill in the art will recognize that the term hydroxyapatite relates to a number of calcium phosphate mineral phases.

Particulate, non-interlinked bioactive glass is preferred in the present invention. That is, the glass is in the form of small, discrete particles, rather than a fused matrix of particles or a mesh or fabric (woven or non-woven) of glass fibers. Note that under some conditions the discrete particles of the present invention may tend to cling together because of electrostatic or other forces but are still considered to be non-interlinked. Preferably the average particle size is less than about 90 microns; more preferably, less than about 20 microns; even more preferably, less than about 5 microns. Particle size, as used herein, is measured by SEM or other optical microscopy techniques, or by laser light scattering techniques (i.e., using a Coulter counter).

The glass composition can be prepared in several ways, to provide melt-derived glass, sol-gel derived glass, and sintered glass particles. The sintered particles may be in sol-gel derived, or pre-reacted melt derived form. Sol-gel derived glass is generally prepared by synthesizing an inorganic network by mixing metal alkoxides in solution, followed by hydrolysis, gelation, and low temperature (less than about 1000° C.) firing to produce a glass. Melt derived glass is generally prepared by mixing grains of oxides or carbonates, melting and homogenizing the mixtures at high temperatures, typically between about 1250 and 1400° C. The molten glass can be fritted and milled to produce a small particulate material.

Suitable bioactive glass/ceramic materials include those described in U.S. Pat. Nos. 4,159,358; 4,234,972; 4,103,002; 4,189,325; 74,171,544; 4,775,646; 4,857,046, and 5,074,916 and 5,735,942, the contents of which are hereby incorporated by reference in their entirety.

Where the term "solution" of bioactive glass is used, this term is intended to include solutions, suspensions and dispersions of bioactive glass. The term "extract" or "bioactive extract" is intended to mean a solution that is made, for example, by reacting bioactive glass particles in an appropriate solvent such as water or tris buffer for an appropriate amount of time, and the solution is then filtered with the resulting particle free solution used to treat nails. The term "extract" or "bioactive extract" is also meant to include any solution that includes silica, sodium, calcium and phosphorus.

II. Formulations Including Bioactive Glass

A. Components

The bioactive glass or extract of bioactive glass may be administered to the nail in a topical formulation, such as in the form of a suspension, lotion, cream (water-in-oil emulsion) or gel, provided that the formulation includes a sufficient amount of water such that the ions can be formed and allowed to react with the nail to form the hydroxyapatite layer. Those skilled in the art will appreciate that there are other appropriate topical carriers such as those listed in the U.S.P.D.

In one embodiment, the carrier includes a hydrophilic polymer. As used herein, a hydrophilic polymer is defined as a polymer with a solubility of greater than one gram per liter. Examples of suitable hydrophilic polymers include polyvinyl alcohol, polyethylene glycol, polyethylene oxide, polyvinylpyrrolidone, poly(ethyloxazoline), poly(ethylene oxide)-co-poly(propylene oxide) block copolymers, polysaccharides or carbohydrates such as hyaluronic acid, dextran, heparan sulgate, chondroitin sulfate, heparin or alginate, and proteins such as gelatin, collagen, albumin, ovalbumin, or polyamino acids. Other suitable polymers include those described in U.S. Pat. No. 5,410,016 to Hubbell, the contents of which are hereby incorporated by reference.

The hydrophilic polymers can include ionically or covalently polymerizable groups, such that the polymers can be crosslinked when applied to the nail surface. This results in a polymerized coating on the nail bed which includes a relatively high concentration of water and enables the coating to remain on the nail for an extended period of time.

In addition to bioactive glass, the formulations can include other therapeutic agents such as antibiotics, antivirals, anti-fungal agents, biotin, collagen, amino acids, proteins, and vitamins. The composition can also include dyes, fragrances and other cosmetically useful additives.

Other components which can be included are penetration enhancers and/or permeation/binding agents as described, for example, in U.S. Pat. No. 5,785,959, the contents of which are hereby incorporated by reference. Examples of penetration enhancers include menthol, propylene glycol, dimethyl sulfoxide, dimethyl acetamide, and azone.

The permeation agents and/or penetration enhancers allow the nail to absorb more water, and accordingly, more of the nail-strengthening ions from the composition. This also allows the composition to penetrate deeper into the nail than would be possible without the permeation enhancer.

B. Proportion of Individual Components

While the ratio of bioactive glass to carrier is not critical, preferably the blend of bioactive glass, other therapeutic agents, and carrier contains about 20% to about 80%, more preferably, about 50% by weight of bioactive glass. The optional components are preferably present in an amount equal to about 10 percent by weight or less of the composition.

III. Articles of Manufacture Including the Composition

A. Two-Part Compositions

It is preferable that the glass not be significantly pre-reacted prior to application to the nails. This can be achieved, for example, by mixing the bioactive glass and water to form the compositions and applying the composition to the nails immediately after mixing.

The bioactive particulate glass and topical carrier can be separate components in a two-part system wherein the bioactive glass and topical carrier are mixed and simultaneously applied. For example, a two part mixing syringe with two separate storage chambers and a mixing chamber can be used. Other two part delivery systems are known to those of ordinary skill in the art.

B. Medicating Devices

In one embodiment, the composition is applied to the nails in the form of a medicating device which includes a viscoelastic gel pad which conforms to the shape of the nail, and which is impregnated with bioactive glass and an aqueous solution, such that the composition remains in contact with the nail for an extended period of time. Suitable medicating devices include those described, for example, in U.S. Pat. No. 5,181,914 to Zook, the contents of which are hereby incorporated by reference.

Allowing the composition to remain in contact with the nail for an extended period of time permits the growth of thicker layers of hydroxyapatite than would be possible with relatively shorter exposure of the nail to the compositions.

IV. Methods for Treating the Nails and Adjacent Tissues

The compositions can be administered to the nails and adjacent tissues for an extended period of time (i.e., several hours), or can be administered over several shorter periods of time (i.e., one or two daily applications for a period of between 1 and 15 minutes, preferably between 5 and 10 minutes). When the composition or extract is in the form of a soak, the nails are placed in the soaking solution and allowed to remain in solution for the desired time period. When the composition is in the form of a gel, the composition can be applied and allowed to remain for longer periods of time, until the gel is ultimately removed from the nails. When the composition is in the form of a medicating device, the composition can be applied and allowed to remain on the nails for an even longer period of time. This method of application can be particularly preferable for overnight applications. After the composition has been in contact with the nails for a sufficient amount of time, the composition can be removed.

The amount of the compositions which is applied, and the duration of the application, is at the discretion of the user. However, the compositions are typically applied by generously spreading the compositions onto the nails at least once a day. After treatment, the nails can be washed, dried, and optionally coated with conventional lacquer nail coatings.

The compositions fill voids in the nails, and fill in the naturally occurring irregular contour of the nail surfaces. The hydroxyapatite layer which results from the application of the compositions can create a desirable surface for adhering traditional nail coatings, such as lacquer coatings, and also increase their durability.

The present invention will be more clearly understood with reference to the following non-limiting examples.

EXAMPLES

Example 1

Application of Bioglass to a Nail Surface 0.2 grams of Bioglass® with a particle size of less than 20 microns was mixed with an equal volume of water to form a paste. The paste was applied to the nails of one hand and allowed to dry. No material was applied to the nails of the other hand. After about three minutes, the excess Bioglass® was wiped off, and a base coat of nail polish was applied to both hands. Following this, two coats of polish was applied to the nails. This procedure was repeated twice a week. After one week, or two applications of the Bioglass® powder, there was a discernable difference in the strength and hardness of the nails treated with the Bioglass® powder, compared to the untreated control. The Bioglass® treated nails were harder, and not as easily bent. The cuticle also appeared to be healthier in appearance. Over a period of two months following the above regimen, there was only one damaged nail on the Bioglass® treated hand, whereas there were at least six broken nails on the untreated hand.

Example 2

Treatment of Nails with a Solution of Bioglass

A nail was exposed to a solution containing 0.3 grams of Bioglass® powder with an average particle size of less than 10 microns, in 200 ml of water. The nail was allowed to soak for a number of time intervals, each approximately 15 minutes in duration, for a total soak time of about 20 hours. Following this exposure, Fourier transform infra-red analysis (FTIR) was performed. The spectra show the formation of an HCA layer on the surface of the nail.

Figure 1B:
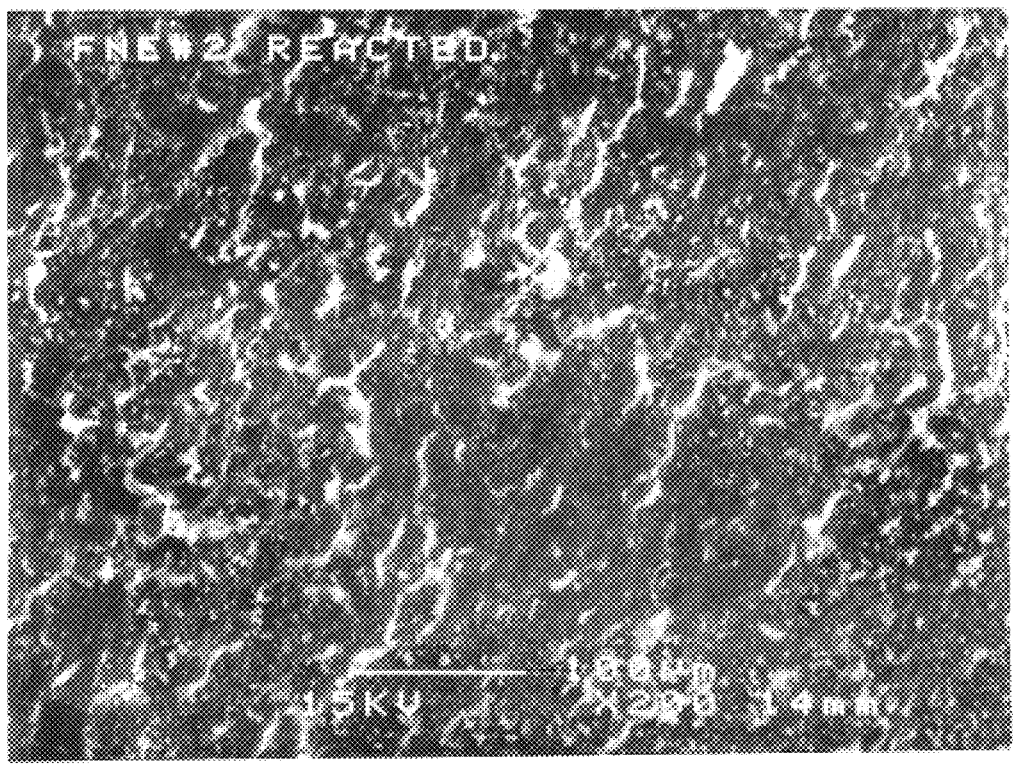
Figure 2A:
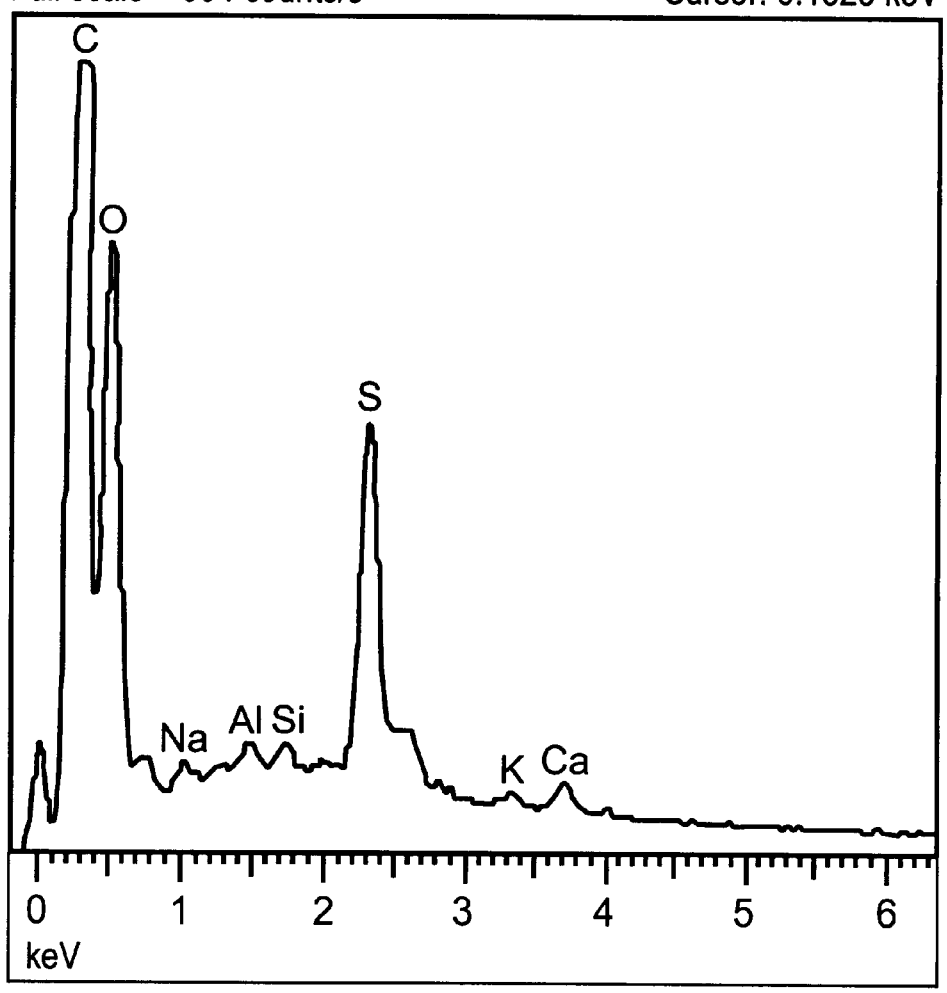
FIGS. 2a and 2b represent the EDS analysis of an un-reacted fingernail surface FIG. 2a) and and a nail treated for 20 hours with a TRIS buffer solution including Bioglass® particles (FIG. 2b).
Figure 2B:
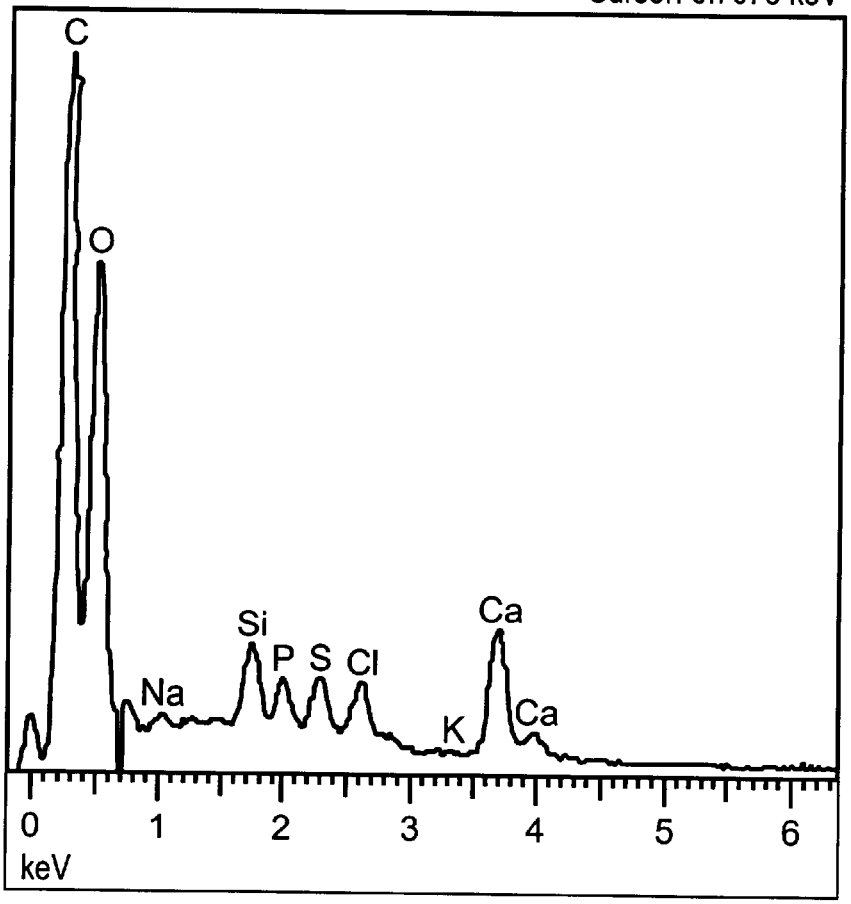

Scanning electron microscopy (SEM) shows the nail surface before and after treatment (200× magnification) (FIGS. 1a and 1b). The surface of the nail prior to treatment shows numerous cracks and defects on the nail surface (FIG. 1a). After treatment (FIG. 1b), the surface of the nail is much smoother, with most of the defects annealed, or covered by the calcium phosphate layer which was formed. The accompanying EDS figures (FIGS. 2a and 2b) show the elemental spectra of the nail surface before and after treatment. FIG. 2a shows the EDS (energy dispersive x-ray analysis) of the nail before treatment, and FIG. 2b shows the EDS of the nail after treatment. Before treatment, the spectra shows a small calcium peak, a large sulfur peak as well as oxygen and carbon peaks, all derived from the nail surface. After treatment, the EDS spectrum shows two new peaks, corresponding to phosphorus and silicon, both of which come from the ions released by the bioactive glass, which formed deposits on the nail surface. In addition, the intensity of the calcium peak increased, indicating the formation of a calcium phosphate layer. This layer largely prevents x-rays from escaping the nail surface because the calcium phosphate absorbs most of the x-rays.

The data shows that, after exposure to the Bioglass® solution, an extensive protective HCA layer formed on the surface of the nail. The layer smoothed the nail surface, filled in gaps in the surface, and covered many irregularities and surface imperfections. The HCA layer protects and strengthens the nail.

Example 3

Treatment of Nails with a Solution Made from Bioglass® Extracts.

An extract solution was made by adding 90 g of <20 μm Bioglass® particulate to 510 ml of a tris buffer solution (tris-hydroxymethyl aminomethane, buffered with HCl to make a 0.1 N solution). The mixture was mixed for 2 hours at room temperature using a magnetic stirrer. The solution was then filtered through a 0.44 μm filter, and the resulting solution contained 15.0 wt. % Bioglass) extract. A set of nails was then exposed to this solution for a total soak time of 20 hours. Following exposure, FTIR was performed. The spectra clearly show the formation of a calcium phosphate layer tightly bound to the nail surface. After treatment the nail surface is smooth, and the number of defects is greatly reduced, when compared to the untreated nail surface.

We claim:

1. A method for treating nails comprising applying a composition comprising an effective, nail-enhancing amount of non-interlinked particles of bioactive glass to the nails for a sufficient amount of time to provide that a layer of hydroxyapatite or other calcium phosphate crystals is formed on the nail and ions from the bioactive glass penetrate layers of the nails to form hydroxyapatite crystals within the layers of the nails.

2. The method of claim 1, wherein the average particle size of the bioactive glass particles is less than about 90 microns.

3. The method of claim 1, wherein the average particle size of the bioactive glass particles is less than about 20 microns.

4. The method of claim 1, wherein the average particle size of the bioactive glass particles is less than about 5 microns.

5. The method of claim 1, wherein the nails are coated with a layer of hydroxyapatite or other calcium phosphate mineral that is at least 0.2 microns thick.

6. The method of claim 1, wherein the composition further includes an aqueous solvent.

7. The method of claim 1, wherein the composition further includes a hydrophilic polymer.

8. The method of claim 1, wherein the composition further includes one or more components selected from the group consisting of antibiotics, antivirals, antifungal agents, biotin, collagen, amino acids, proteins, vitamins, penetration enhancers, permeation/binding agents, dyes, and fragrances.

9. The method of claim 1, further comprising removing the bioactive glass from the nail surface.

10. The method of claim 9, further comprising applying a protective lacquer coating on the nails following removal of the bioactive glass from the nail surface.

11. A medicating device for application to the nails comprising a viscoelastic gel pad which conforms to the shape of the nail, wherein the pad is impregnated with non-interlinked particles of bioactive glass and an aqueous solution.

12. The device of claim 11, further comprising one or more components selected from the group consisting of antibiotics, antivirals, antifungal agents, biotin, collagen, amino acids, proteins, vitamins, penetration enhancers, permeation/binding agents, dyes, and fragrances.

13. A method of treating nails comprising applying the medicating device of claim 11 to the nails for a sufficient amount of time to form a layer of hydroxyapatite or other calcium phosphate minerals that is at least about 0.2 microns in thickness.

14. A method for treating nails in mammals other than humans comprising applying a composition comprising an effective, nail-enhancing amount of non-interlinked particles of bioactive glass to the nails for a sufficient amount of time to provide that a layer of hydroxyapatite or other calcium phosphate crystals is formed on the nails and ions from the bioactive glass penetrate layers of the nails to form hydroxyapatite crystals within the layers of the nails.

15. The method of claim 14 wherein said mammals are dogs or cats.

16. A method for treating nails comprising applying a composition comprising an effective, nail-enhancing amount of bioactive extract to the nails for a sufficient amount of time to provide that a layer of hydroxyapatite or other calcium phosphate crystals is formed on the nails and ions from the bioactive extract penetrate layers of the nails to form hydroxyapatite crystals within the layers of the nails.

* * * * *